United States Patent [19]

Filomeno

[11] Patent Number: 4,792,443
[45] Date of Patent: Dec. 20, 1988

[54] SKIN BLEACHING PREPARATIONS

[75] Inventor: Vito G. Filomeno, Mt. Arlington, N.J.

[73] Assignee: Warner-Lambert Company, Morris Plains, N.J.

[21] Appl. No.: 55,677

[22] Filed: May 29, 1987

Related U.S. Application Data

[63] Continuation-in-part of Ser. No. 811,602, Dec. 20, 1985, Pat. No. 4,692,261.

[51] Int. Cl.$^4$ ............................................. A62K 7/135
[52] U.S. Cl. ..................................... 424/62; 252/404
[58] Field of Search ...................... 252/94, 105, 404; 424/62; 514/549, 728

[56] References Cited

U.S. PATENT DOCUMENTS

| | | | |
|---|---|---|---|
| 3,855,150 | 12/1974 | Weris | 252/404 |
| 3,856,934 | 12/1974 | Kligman | 424/62 |
| 4,025,645 | 5/1977 | Jelenko | 514/549 |
| 4,051,257 | 9/1977 | Jelenko | 514/549 |
| 4,136,166 | 1/1979 | Barnett et al. | 424/62 |
| 4,466,955 | 8/1984 | Calvo et al. | 424/62 |
| 4,490,330 | 12/1984 | Howes et al. | 422/29 |

FOREIGN PATENT DOCUMENTS

85/04101 9/1985 World Int. Prop. O. .

OTHER PUBLICATIONS

McCutchen's "Functional Materials," 1981, p. 23

*Primary Examiner*—Prince E. Willis
*Attorney, Agent, or Firm*—Henry C. Jeanette; Gary M. Nath

[57] ABSTRACT

A skin bleaching skin preparation is disclosed. The preparation comprises hydroquinone, tertiary butyl hydroquinone, and optionally an additional stabilizer. The preparation can additionally contain a buffer to maintain the pH between about 3.5 and about 7.5. By maintaining this pH range in the presence of the tertiary butyl hydroquinone stabilizer, and optional additional stabilizers, the hydroquinone would not be oxidized, and thus the preparation would be characterized by an extended shelf life.

8 Claims, No Drawings

SKIN BLEACHING PREPARATIONS

REFERENCE TO RELATED APPLICATION

This application is a continuation-in-part of copending application Ser. No. 811,602, filed Dec. 20, 1985, now U.S. Pat. No. 4,692,261 the disclosure of which is incorporated herein by reference thereto.

BACKGROUND OF THE INVENTION

This invention is concerned with a detergent bar containing hydroquinone as a skin bleaching ingredient.

Melanin is a dark, sulfur-containing pigment normally found in the skin, hair, eyes and certain nerve cells which is produced in cells called melanocytes. Melanin is produced in the melanocytes by the conversion of the amino acid tyrosine in the presence of the enzyme tyrosinase. It is generally believed that the number of melanocytes varies widely among individuals.

There frequently occurs in a given individual a localized area of the skin wherein the melanin density within the melanocytes is markedly increased resulting in a skin color in the area affected far darker than normal background skin color. These localized areas of hyperpigmentation are commonly referred to as Brown Spots, Age Spots or Liver Spots. Women are also subject to these melanin-dense spots as a result of child bearing and taking birth control pills. The skin disfigurement which results from these areas of hyperpigmentation, which may be more or less permanent in character, is often a source of great distress to the individual.

In the past there have been described a number of topical skin compositions containing one or more ingredients capable of reducing the melanin density in the melanocytes of the skin. Such ingredients are termed depigmentation agents or bleaching agents and are absorbed into the lower layers of the skin in order to inhibit the formation of melanin in the melanocytes.

The most frequently described bleaching agents are based on hydroquinone or derivatives of hydroquinone, Benzyloxyphenol, the monobenzylether of hydroquinone, is one such hydroquinone derivative which has found wide application as a bleaching agent. In U.S. Pat. No. 3,060,097 for example, a skin bleaching composition is described comprising benzyloxyphenol, sodium hypochlorite, a penetrant and a soothing agent such as a lanolin compound and a solvent acting also as a penetrant. Unfortunately benzyloxyphenol is not metabolized to any great degree when absorbed into the skin and is associated with incidents of irreversible depigmentation simulating vitiligo (patches of depigmentation often having a hyperpigmented border and enlarging slowly). In addition bezyloxyphenol is transported by the lymph system and may cause irreversible depigmentation in areas of the body far removed from the site of application. Methoxyphenol, another ether of hydroquinone, has also been used in cosmetic compositions for depigmentation but is relatively insoluble in the aqueous media which is a constituent of many cosmetic formulations.

A substituted isomer of hydroquinone, 4-isopropyl catechol has also been employed as the active ingredient in cosmetic formulations to effect skin depigmentation (see South African Pat. Appl. No. 716,890). Mono- and di-fatty acid esters of hydroquinone have also been employed in topical skin depigmentation compositions and are described in European patent Application No. 82301102.8.

Hydroquinone itself is conveniently used in cosmetics for the treatment of hyperpigmentation since it is effective, soluble in water and readily metabolized and excreted from the body. Hydroquinone, however, when present in an alkaline environment is unstable and is oxidized to the quinone form imparting an accompanying browning effect to any composition in which it is incorporated. To prevent such oxidation it is necessary to incorporate an antioxidant into the hydroquinone-containing composition such as ascorbic acid or butylated hydroxy anisole to modify the hydroquinone itself. Hydroquinone is also a skin irritant.

Alcoholic-gel cosmetic sticks such as stick deodorants offer a medium for cosmetic bleaching using hydroquinone since it is soluble in alcohol. However, the gelling agents used in such sticks are soaps such as sodium stearate and their alkalinity readily and rapidly decomposes hydroquinone.

Hydroquinone has also been estabilized by incorporating it into an anhydrous medium. In U.S. Pat. No. 4,466,955, a non-aqueous cosmetic skin preparation is described in which hydroquinone is dissolved in polypropoxylated or polyethoxylated fatty ethers and this anhydrous solution is incorporated into an extended oil and wax non-aqueous cosmetic base. In such an anhydrous oil-wax base the hydroquinone is more stable and less prone to oxidation since oxygen is less soluble in waxes than in water and oxygen from the air does not reach the wax-dissolved hydroquinone as readily as if it were solubilized in water. The polyalkoxylated agents act as solubilizing agents in the hydroquinone and are themselves cosmetic skin penetration agents which allow controlled release of hydroquinone.

The present invention, on the other hand, provides a non-cosmetic synthetic detergent bar for use on the skin containing hydroquinone as a depigmentation agent and water which is maintained at acid to neutral pH to prevent oxidation of the hydroquinone. The bar is characterized by having a long shelf life.

SUMMARY OF THE INVENTION

The synthetic detergent bar of the invention comprises a compressed mixture of synthetic detergents, hydroquinone as the depigmentation agent, a stabilizer for the hydroquinone, water, and a buffer to maintain the pH of the bar from about 4 to 7. The bar also contains excipients such as paraffin, waxes, dextrin, starches and other ingredients.

The synthetic detergents employed in the bar of the invention are anionic detergents which are active and stable at low pH's and non-irritating to the skin. The preferred detergents are coconut-oil fatty acid esters of sodium isethionate and sodium methyl taurate such as sodium cocoyl isethionate and sodium methyl cocoyl taurate; acyl N-methyltaurides; fatty alcohol sulfates; monoalkyl sulfosuccinates; alkyl sulfoacetates such as sodium lauryl sulfoacetate; glyceryl easter sulfates; and acylglutamates, among others. A mixture or blend of these compounds is also suitable. Generally the amount of detergent should comprise from 20 to 45% by weight of the total bar and preferably from 25% to 30% by weight. By avoiding conventional soap formulations which are blends of fatty acids and alkali high pH's are avoided which contribute to hydroquinone oxidation. The use of these synthetic detergents makes it feasible to formulate the bar at a lower pH, thus maintaining the chemical stability of hydroquinone.

The hydroquinone is incorporated into the bar in amounts to effect depigmentation. Generally amounts of between 1% and 5% by weight of the total bar and preferably about 1.5 to about 3.0% and most preferably 2% by weight are suitable.

Water is employed in the bar formulation at levels of from 15% to 20% by weight of the total bar and preferably between about 10% and 15% by weight. The water serves to dissolve the hydroquinone and acts as a binder and plasticizer.

In order to maintain the pH of the bar at about 4 to about 7 and thus to enhance hydroquinone stability a buffer is dissolved in the water. Such buffers include citric acid, lactic acid or other similar organic acid.

Generally the buffer should comprise from about 1% to 5% by weight of the total bar and preferably about 2% by weight.

To further maintain the stability of the hydroquinone against oxidation a stabilizer is added to the bar composition. Of particular effectiveness as a stabilizer is tertiary butyl hydroquinone (TBHQ). The tertiary butyl hydroquinone may be used alone or in combination with other stabilizers such as sodium sulfite, sodium bisulfite and alpha tocopherol. The sulfite, bisulfite and tocopherol stabilizers are effective but not to the degree of TBHQ. Generally the total amount of stabilizer or combinations thereof should not exceed about 0.6% by weight of the total bar. When TBHQ is used in combination with other stabilizers each component stabilizer should be present in amounts between 0.1% and 0.3% by weight of total bar.

Other ingredients such as paraffin, waxes, starches and dextrin are added to the bar to provide desirable physical and aesthetic qualities. These ingredients should constitute between 50% and 60% by weight of the bar.

The paraffin ingredient is preferably a fully refined petroleum wax having a melting point ranging from about 130° F. to about 140° F. This wax is odorless and tasteless and meets FDA requirements for use as coatings for food and food packages. Such paraffins are readily available commercially. A very suitable paraffin can be obtained, for example, from the Standard Oil Company of Ohio under the tradename Factowax R-133.

The paraffin ingredient is used in the product to impart plasticity, firmness, and processability in soap equipment. It also provides a glossy look and smooth feel to the bar.

The paraffin ingredient is optionally supplemented by a microcrystalline wax. A suitable microcrystalline wax has a melting point ranging, for example, from about 140° F. to about 160° F., preferably from about 145° F. to about 155° F. The wax preferably should meet the FDA requirements for food grade microcrystalline waxes. A very suitable microcrystalline wax was obtained from Witco Chemical Company under the tradename Multiwax X-145A. The microcrystalline wax preferably is present in the bar in an amount ranging from about 0.5% to about 5% by weight. The microcrystalline wax ingredient imparts pliability to the bar at room temperatures.

The combination of powdered starch and dextrin ingredients provide a unique filler system to help provide, with the waxes, a base to carry the detergent.

The powdered starch ingredient is preferably selected from the group consisting of pregelatinized starch and non-gelling starch, and very preferably the total starch ingredient used is present in the bar in an amount ranging from about 7.5% to about 13.5% by weight. The pregelatinized starch is preferably a gelling pregelatinized starch as precooked corn starch which has been dried and powdered. A very suitable gelling pregelatinized starch is obtained from CPC International under the tradename Amidex (B-511). The gelling pregelatized starch is very tacky, providing binding and imparting slip feel to the bar. This starch works particularly well when coconut-oil fatty acid ester of sodium isethionate is used as a detergent ingredient. The non-gelling starch is preferably a 100% amylopectin starch. A very suitable 100% amylopectin starch is obtained from National Starch under the tradename Amioca. The 100% amylopectin starch imparts very desirable processing characteristics to the formula. This starch works particularly well when sodium lauryl sulfoacetate is used as a detergent ingredient. The two types of starches can be used in conjunction with other in a total amount within the aforedescribed broad range to help provide optimum slip-feel and processability. A bar including both types of starches can include, for example, from about 5% to about 10% by weight gelling pregelatinized starch and from about 2% to about 4% by weight non-gelling 100% amylopectin starch.

The dextrin ingredient is dextrin having a water solubility ranging from about 25% to about 85% (about 25% to about 85% by weight of the dextrin dissolves in water, and the rest is insoluble). Very preferably, the total amount of dextrin used is present in the bar in an amount ranging from about 12.5% to about 25% by weight. Very preferably, the dextrin ingredient is selected from the group consisting of dextrin having a water solubility ranging from about 25% to about 55%, and dextrin having a water solubility ranging from about 60% to about 85%. Dextrin having a water solubility ranging from about 25% to about 55%, with its higher insoluble content, can be used to control washing wear rate and to improve processability. A dextrin of this type is obtained from National Starch and chemical Corporation under the tradename Nadex 341 (it is a white powdered corn dextrin and has an average water solubility of about 40%). Dextrin having a water solubility ranging from about 60% to about 85% imparts a smooth slip-feel to the bar but introduces higher washing wear rate and tends to lower processability. A dextrin of this type is obtained from National Starch and Chemical corporation under the tradename Nadex 419 (it is a white powdered corn dextrin and has an average water solubility of about 70%). By using these two types of dextrins in conjunction (both types together being used in a total amount within the aforedescribed broad range), optimum conditions can be achieved for bar feel, washing wear rate and processability. Very preferably, the two types of dextrins are used in conjunction with each other in the same bar, and dextrin having a water solubility ranging from about 25% to about 55% is present in the bar in an amount ranging from about 2% to about 20% by weight and dextrin having a water solubility ranging from about 60% to about 85% is present in the bar in an amount ranging from about 5% to about 20% by weight with the total of the two types of dextrin being present in the bar in an amount ranging from about 12.5% to about 25% by weight. The dextrin water solubilities herein are in 72° F. water.

Sodium chloride is optionally included. It is used for example, at a level ranging from about 0.5% to about 4% by weight, for processing purposes. It is, for example, of positive assistance in making a premix of water and powdered starch(es) before crutcher mixing (see processing described below).

The pH of the bar preferably falls in a range of about 4.5 to about 6.5.

While bars produced according to this invention have demonstrated no deterioration due to bacterial activity, it is recognized that dextrin content particularly can support bacterial growth. To obviate this possibility, antimicrobials, e.g., methyl and propyl parabens, can optionally be included, for example, at a level ranging from about 0.25% to about 1% by weight.

Added bar slip-feel is readily obtained by incorporating such agents as high molecular weight polymers of ethylene oxide (e.g. a polymer acid under the tradename Polyox WSR 205 by Union Carbide) and high molecular weight polymers of acrylamide (e.g., a polymer sold under the tradename Gelamide F by American Cyanamid).

The ingredients can be processed to form bars using conventional soap line equipment. For example, processing can be carried out as follows. First, premelted waxes (microcrystalline wax, if any is used, and paraffin) are added to the the crutcher. Lauric diethanolamide may be also added into the crutcher in premelted form. The temperature in the mix is then adjusted to be in the 109° F.–200° F. range. Next, the powdered detergent is added and this lowers the temperature of the mix. The crutcher agitation is started and heat is supplied. This is continued until a smooth slurry is obtained at 160° F.–180° F. Next, the dextrins are introduced. Then crutcher agitation is started again, and heating is supplied; this is continued until a uniform slurry is obtained at 160° F.–180° F. Then, a pre-mixed powdered starch water slurry is added, and again crutcher agitation is continued and heat is supplied until the total contents are uniform at 160° F.–180° F. Lactic or other acid (to modify bar pH) is readily added with the starch water slurry. Following this the temperature is lowered and the hydroquinone stabilizers are added and mixed. The resulting mix is dropped on a cold roll and taken off in the form of a chip or flake. These (chips or flakes) are passed through a plodder. The effluent from the plodder is collected in soap buggies. The buggies feed the conventional soap equipment line consisting of an amalgamotor, mills, vacuum plodder and soap press.

Bars formulated in accordance with the present invention show minimal discoloration after storage for 3 months or more. Assays of hydroquinone in these bars indicated minimal oxidation.

The effective stabilization of hydroquinone with TBHQ and, optionally, another hydroquinone stabilizer, in the detergent bars described herein, may also be effective in a variety of other well known skin and cosmetic preparations or bases. Therefore, the stabilized skin bleaching system of hydroquinone with TBHQ and, optionally, the other stabilizers disclosed above may be used in any skin preparation or base having a pH of about 3.5 to about 7.5. The preparations comprising the stabilized skin bleaching system are yet another aspect of this invention.

The skin preparations (i.e., any composition suitable for use on the skin) utilizable include, but are not limited to, lotions, creams, wax based sticks, aerosols, alcohol sticks, and the like. The formulation of these preparations, to which the stabilized system of this invention may be added, are well known to those skilled in the art. For example, see Balsam, M. S., and Sagarin, E. (Editors), *Cosmetics Science and Technology*, Second Edition, Volumes 1 and 2, Wiley - Interscience, a division of John Wiley & Sons, Inc., New York, copyright 1972; Sagarin, E. (Editor), *Cosmetics Science and Technology*, Interscience Publishers, a division of John Wiley & Sons, New York, copyright 1957; and "Cosmetics", In: *Kirk-Othmer Encyclopedia of Chemical Technology*, Third Edition, Volume 7, pages 143–176, A Wiley-Interscience Publication, John Wiley & Sons, New York, copyright 1979; the disclosures of each being incorporated herein by reference thereto. Also see, for example, Wilkinson, J. B., Moore, R. J. (Editors), *Harry's Cosmetology*, Seventh Edition, Chemical Publishing, New York, copyright 1982, the disclosure of which is incorporated herein by reference thereto. The various components of these skin preparations, e.g. emulsifiers, waxes, emollients, thickening agents, phase modifiers and the like, may be suitably varied in accordance with the desired end product. These components may be selected from well known ingredients, including those amongst the listings in Estrin, N. F., Crosley, P. A., and Haynes, C. R. (Editors), *CTFA Cosmetic Ingredient Dictionary*, published by The Cosmetic, Toiletry and Fragrance Association, Inc., Washington, D.C., copyright 1982, the disclosure of which is incorporated herein by reference thereto.

Thus, another aspect of this invention provides a skin bleaching skin preparation (composition) comprising:
(a) hydroquinone in amounts to effect depigmentation; and
(b) tertiary butyl hydroquinone in amounts to maintain the stability of said hydroquinone against oxidation.

Yet another aspect of this invention provides a skin bleaching skin preparation comprising:
(a) hydroquinone in amounts to effect depigmentation;
(b) tertiary butyl hydroquinone in amounts to maintain the stability of said hydroquinone against oxidation; and
(c) an additional stabilizer in amounts to maintain the stability of said hydroquinone against oxidation.

The hydroquinone is incorporated into the skin preparation formulation in amounts to effect depigmentation. Generally, amounts of about 1% to about 5% by weight of the total composition are used with about 1.5% to about 3.0% by weight being preferred and about 2% by weight being most preferred.

The tertiary butyl hydroquinone (TBHQ) stabilizer is used in amounts to maintain the stability of said hydroquinone. When used as the only hydroquinone stabilizer TBHQ is generally used in amounts of about 0.1% to about 0.5% by weight of the total composition with about 0.1% to about 0.25% by weight being preferred. When TBHQ is used in combination with another hydroquinone stabilizer the total amount of hydroquinone stabilizers generally should not exceed about 0.6% by weight of the total composition. Stabilizers which can be used in combination with TBHQ include those selected from the group consisting of sodium sulfite, sodium bisulfite, tocopherals including alpha tocopheral, and mixtures thereof. Generally, the stabilizer used in combination with the TBHQ is used in amounts of about 0.05% to about 0.3% by weight of the total composition such that, as stated previously, the total amount of stabilizers in the composition does not exceed about 0.6% by weight. Generally, stabilizers such as sodium sulfite and sodium bisulfite are used in amounts of about 0.05% to about 0.3% by weight and stabilizers such as alpha tocopherol are used in amounts of about 0.1% to about 0.3% by weight.

Generally, as stated previously, buffers are utilized to maintain the pH of the composition. Usually, the pH is at about 3.5 to about 7.5 with about 4 to about 7 being preferred and about 3.5 to about 6 being more preferred. It will be appreciated that for anhydrous formulations, such as waxed based sticks, there essentially is no meaningful pH. Any suitable buffer known in the art may used in an amount to provide the desired buffering capacity.

These skin preparations may be formulated using procedures well know to those skilled in the art. Temperature ranges used for mixing ingredients together and length of times for blending (mixing) the ingredients together are suitably chosen to provide the optimum conditions for the particular ingredients being used. The determination of such parameters are well within the capabilities of those skilled in the art without the need for undue experimentations.

Generally, the hydroquinone stabilizer system can be added at any convenient time during the formulation of the skin preparation. For example, the stabilizer system can be dissolved in the aqueous phase prior to the aqueous phase's addition to the skin preparation, or the hydroquinone stabilizer system can be added to the formulation as a separate component after the addition of all other ingredients. The hydroquinone can be added in a dry state or as a stabilized buffer solution. Whether the hydroquinone is added as a separate component, or whether the hydroquinone is added dissolved in the aqueous phase or dissolved in a stabilized buffer solution, the hydroquinone is generally added last. Thus, first the buffers, if any, are added, followed by the addition of TBHQ and any other additional optional stabilizer which is then followed by the addition of the hydroquinone.

The components utilized in the formulation of the skin preparations can vary in accordance with the type of preparation formulated—e.g., lotions, creams, sticks, aerosols, and the like. Such components can be selected from emollients, emulsifiers, humectants, preservatives, thickeners and film formers, barrier agents, solidifying ingredients, and the like. In selecting the appropriate components (ingredients) care is usually given to selecting those ingredients which are saturated and free from residual peroxides. Ingredients containing double bonds (unsaturation) or residual peroxides (e.g., from the formation of ethoxylated compounds) may prove suitable under the appropriate pH and stabilized conditions. The selection of the appropriate components for the skin preparations of interest is well within the capabilities of those skilled in the art without the need for undue experimentation.

Representative examples of emollients include, for example,

1. Hydrocarbon oils and waxes, such as, mineral oil, petrolatum, paraffin, ceresin, ozokerite, microcrystalline wax, polyethylene, perhydrosqualene (squalane), and the like;

2. Silicone oils, such as, dimethyl polysiloxanes, methylphenyl polysiloxanes, water-soluble and alcohol-soluble silicone glycol copolymers, and the like;

3. Triglyceride esters, such as, vegetable and animal fats and oils, and the like;

4. Acetoglyceride esters, such as, acetylated monoglycerides, and the like;

5. Ethoxylated glyceride, such as, ethoxylated glyceryl monostearate, and the like;

6. Alkyl esters, such as, methyl, isopropyl, and butyl esters of fatty acids; hexyl laurate, isohexyl laurate, isohexyl palmitate, decyl oleate, isodecyl oleate, hexadecyl (isocetyl) stearate, diisopropyl adipate, diisohexyl adipate, dihexadecyl adipate, diisopropyl sebacate, lauryl lactate, myristyl lactate, cetyl lactate, and the like;

7. Alkenyl esters, such as, oleyl myristate, oleyl stearate, and oleyl oleate, and the like;

8. Fatty acids, such as, pelargonic, lauric, myristic, palmitic, stearic, isostearic, hydroxystearic, arachidic, behenic, erucic, lanolin acids, and the like;

9. Fatty alcohols, such as, lauryl, myristyl, cetyl, hexadecyl (isocetyl), stearyl, isostearyl, hydroxystearyl, oleyl, ricinoleyl, behenyl, erucyl, 2-octyl dodecanol, lanolin alcohols, and the like;

10. Fatty alcohol ethers, such as, ethoxylated lauryl, cetyl, stearyl, isostearyl, oleyl, cholesterol, and lanolin alcohols; propoxylated cetyl, oleyl, and lanolin alcohols, and the like;

11. Ether-esters such as, fatty acid esters of ethoxylated fatty alcohols, and the like;

12. Lanolin and derivatives, such as, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis (hydrogenation) of lanolin, ethoxylated hydrogenated lanolin, ethoxylated sorbitol lanolin, and liquid and semisolid lanolin absorption bases, and the like;

13. Polyhydric alcohols (polyols) and polyether derivatives, such as, propylene glycol, dipropylene glycol, polypropylene glycol 2000, 4000, polyoxyethylene polyoxypropylene glycols, polyoxpropylene polyoxyethylene glycols, glycerol, ethoxylated glyerol, propoxylated glycerol, sorbitol, ethoxylated sorbitol, hydroxypropyl sorbitol, polyethylene glycol 200–6000, methoxy polyethylene glycols 350, 550, 750, 2000, 5000, poly-[ethylene oxide] homopolymers (mol. wt. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivative of trimethylolpropane, and the like;

14. Polyhydric alcohol (polyol) esters, such as, ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid ester, and the like;

15. Wax esters, such as, lanolin (de-oiled wax fraction), beeswax, spermaceti, myristyl myristate, stearyl stearate, and the like;

16. Beeswax derivatives, such as, polyoxyethylene sorbitol beeswax; these are reaction products of beeswax with ethoxylated sorbitol of varying ethylene oxide content, forming a mixture of ether-esters; and the like;

17. Vegetable waxes, such as, carnauba, candelilla, and the like;

18. Sterols, such as, cholesterol, cholesterol fatty acid esters, and the like;

19. Amides, such as, fatty acid amides, ethoxylated fatty acid amides, solid fatty acid alkanolamides, and the like; and 20. Mixtures thereof.

Representative examples of emulsifiers include, for example,

1. Anionic emulsifiers, including, for example, (a) fatty acid soaps, such as, potassium stearate, sodium stearate, ammonium stearate, triethanolamine stearate, and the like; (b) polyol fatty acid monoesters containing fatty acid soaps, such as, glyceryl monostearate containing either potassium or sodium soap, and the like; (c) sulfuric esters (sodium salts), such as, sodium lauryl sulfate, sodium cetyl sulfate, and the like; (d) polyol fatty acid monoesters containing sulfuric esters, such as, glyceryl monostearate containing sodium lauryl sulfate, and the like; mixtures thereof; and the like;

2. Cationic emulsifiers, based on quaternary ammonium, morpholinium, pyridinum, and imidazolinium salts, and including, for example, (a) N(stearoyl colamino formylmethyl) pyridinium chloride; N-soya-N-ethyl morpholinium ethosulfate; (b) alkyl dimethyl benzyl ammonium chloride; (c) diisobutylphenoxyethoxy ethyl dimethyl benzyl ammonium chloride; (d) cetyl pyridinium chloride; mixtures thereof; and the like; and 3. Nonionic emulsifiers, including, for example, (a) polyoxyethylene fatty alcohol ethers, such as, polyoxyethylene lauryl alcohol, and the like; (b) polyoxypropylene fatty alcohol ethers, such as, propoxylated oleyl alcohol, and the like; (c) polyoxyethylene fatty acid esters, such as, polyoxyethylene stearate, and the like; (d) polyoxyethylene sorbitan fatty acid esters, such as, polyoxyethylene sorbitan monostearate, and the like; (e) sorbitan fatty acid esters, such as, sorbitan monostearate, and the like; (f) polyoxyethylene glycol fatty acid esters, such as, polyoxyethylene glycol monostearate, and the like; (g) polyol fatty acid esters, such as, glyceryl monostearate, propylene glycol monostearate, and the like; ethoxylated lanolin derivatives, such as, ethoxylated lanolin, ethoxylated lanolin alcohols, ethoxylated chlolesterol, and the like; mixtures thereof; and the like;

4. Amphoteric surface active agents derived from fatty imidazolines; and the like; and 5. Mixtures thereof.

Other representative examples of various other ingredients useful in various skin preparation include:

1. Materials for rendering the compositions opaque, such as, zinc oxide, titanium dioxide, magnesium stearate, zinc stearate, hydrous lanolin, mixtures thereof, and the like;

2. Preservatives, such as, methyl and propyl parabens, and the like;

3. Thickeners and film formers, including, (a) plant hydrocolloids, such as, alginates, arabic (acacia), guar, Irish Moss (carrageenan), karaya, locust bean (carob), pectin, quince seed, tragacanth, mixtures thereof, and the like; (b) biosynthetic, such as, a linear polysaccharide xanthan gum, molecular weight in excess of one million, and the like; (c) cellulose derivatives, such as, methylcellulose, hydroxypropylmethylcellulose, sodium carboxymethylcellulose, hydroxyethylcellulose, hydroxypropylcellulose, microcrystalline cellulose, mixtures thereof, and the like; (d) synthetic high polymers, such as, carboxy vinyl polymer, polyvinyl alcohol, mixtures thereof, and the like; (e) clay thickeners, such as, colloidal magnesium aluminum silicate, magnesium aluminum silicate, hydrous magnesium silicate, mixtures thereof, and the like; (f) polyvinylpyrrolidone; and (g) mixtures thereof;

4. Coloring agents;

5. Perfumes;

6. Solidifying agents (for solid products for example) including hard soaps, such as sodium stearate; fatty alcohols; rosin soaps; candelilla wax; beeswax; carnuba wax; mixtures thereof; and the like;

7. Nonvolatile Solvents, such as, a polyhydric alcohol, including, propylene glycol, sorbitol, glycerol, polyethylene glycol 300 or 400, 1,3-butylene, 2-ethyl-1,3-hexanediol, mixtures thereof, and the like; and fatty acid esters, such as, isopropyl palmitate or myristate, and the like;

8. Propellents for aerosols including (a) fluorinated hydrocarbons; (b) hydrocarbons, such as, propane, butane, isobutane, dimethyl ether, and mixtures thereof, and the like; (c) gases, such as, nitrogen, nitrous oxide, carbon dioxide, and the like; (d) chlorinated compounds, such as methylene chloride, methyl chloroform, and the like; (e) and the like;

9. and the like.

By using effective amounts of the exemplified components various types of creams, lotions, solid sticks, and aerosol formulations, can be blended in accordance with known compositions and procedures. Thus, for example cleansing creams of the beeswax-borax emulsion type may be formulated from beeswax, mineral oil, borax and water. Usually the mineral oil used is a light to medium mineral oil. Generally borax is used in the stoichiometric quantity necessary to neutralize the free acids present in beeswax. Additional ingredients may be added from the following: spermaceti (as an emollient and to make the cream opaque); cetyl alcohol (emollient and emulsion stabilizer); paraffin (makes cream firm and quick melting); petrolatum (increases body & stabilizes); ozokerite (stiffens cream); ceresin (stiffens cream); vegetable oils (emollient); cocoa butter (skin softener); and lanolin (emollient).

A liquefying cleansing cream may be formulated from a mixture of oils and waxes. For example, a physical mixture of mineral oil, paraffin, petroleum & other waxes may be melted, mixed and poured while warm. Emollients may be added (e.g., lanolin or its derivatives, cetyl alcohol, spermaceti, cocoa butter, and the like) along with opaque forming compounds selected from the group consisting of zinc oxide, titanium dioxide, magnesium stearate, hydrous lanolin, and the like.

Emulsion type creams, rather than using the beeswax-borax system, maybe formulated from emulsifiers such as sorbitan fatty acid esters and their polyoxyethylene derivatives, glycerol monostearate, diethylene glycol monostearate, sodium cetyl sulfate, and the like.

Acid-containing cleansing creams may be formulated from emulsifying agents such as lanolin, lanolin absorption bases, wool waxes, pure glyceryl monostearate in conjunction with sapamines, pure diglycol stearate with fatty alcohol sulfates, partially phosphated fatty alcohols, and cetyl or stearyl alcohols, and the like. The acidic substances may be selected from citric acid, lactic acid, lemon juice, and the like.

Cleansing lotions may be formulated as a simple emulsion or solution of a detergent in water. This type of lotion may be an oil-in-water emulsion containing an oil, emulsifying agent (emulsifier), and auxiliary emulsifiers. The emulsifying agent may be triethanolamine stearate and the auxiliary emulsifiers, for example, may be selected from the group consisting of: glycerol monostearate, fatty alcohols, stearic acid, beeswax, and mixtures thereof.

Emollient lotions use oils and waxes identical to that of an emollient cream but are lower in concentration. Emollient lotions may be formulated from emollient oils, emolient waxes and wax like thickeners, polyhydric alcohols, emulsifying agents, and thickeners. The emollient oils would include liquid hydrocarbons, silicones, vegetable and animal fats and oils, alkyl esters, lanolin and derivatives, lecithin derivatives, and the like. The emollient waxes would include beeswax, spermaceti, and solid hydrocarbons, and they are used primarily as oil phase thickener. The wax like thickeners would include cetyl and stearyl alcohol, glyceryl monostearate, sorbitan monostearate, ethylene glycol monostearate, and polyethylene glycol 400 distearate. The polyhydric alcohols include propylene glycol, glycerol, sorbitol, and poyoxyethylene sorbitol. The thickeners would include the plant hydrocolloids, biosynthetic, cellulose derivatives, synthetic high-polymers and clay thickeners.

Hand creams and lotions may be formulated from emollients, barrier agents, humectants, thickeners and film formers, emulsifiers, preservatives, perfume oils, coloring agents and other formulation ingredients.

Solid sticks may be formulated using ethyl alcohol (e.g., ethyl alcohol SD-39C or -40) a solidifying ingredient, optionally a polyhydric alcohol and water and other formulation ingredients. Prepared alcoholic based sticks should be placed in air-tight containers to prevent evaporation of the alcohol because such evaporation could result in shrinkage of the product.

To these formulations the skin bleaching stabilized system of this invention may be incorporated with the use, if necessary, of buffers to maintain the pH between about 3.5 and 7.5.

In order to more completely describe the present invention the following Examples are provided. Such Examples are given to demonstrate specific embodiments of the invention and do not limit the scope of the invention.

EXAMPLES 1-3

These Example demonstrate the preparation of a synthetic detergent bar containing hydroquinone as the depigmentation agent and also demonstrates the efficacy of tertiary butyl hydroquinone as the preferred stabilizer.

In all Examples a detergent bar was prepared by the procedure described above. In Example 1 a mixture of tertiary butyl hydroquinone, sodium sulfite and sodium bisulfite was employed as the stabilizer; in Example 2 only sodium sulfite and sodium bisulfite was employed and in Example 3 alpha tocopherol was employed as the sole stabilizer. The active synthetic detergents were sodium cocoyl isethionate and sodium lauryl sulfoacetate in all Examples. Paraffin, waxes, dextrin and starches were also added. Table 1 below lists the ingredients and, corresponding amounts in weight percent of the bar.

TABLE 1

| Ingredient | 1 | 2 | 3 |
|---|---|---|---|
| Cocyl Isethionate | 28.00 | — | — |
| Sodium Lauryl Sulfoacetate | — | 28.00 | — |
| Combination * of detergents | — | — | 28.00 |
| Water | 15.00 | 15.00 | 15.00 |
| Hydroquinone | 2.00 | 2.00 | 2.00 |
| Buffer | 2.00 | 2.00 | 2.00 |
| Sodium Sulfite | 0.30 | 0.30 | — |
| Sodium Bisulfite | 0.20 | 0.20 | — |
| Tertiarybutyl Hydroquinone (TBHQ) | 0.10 | — | — |
| Alpha Tocopherol | — | — | 0.20 |
| Waxes, Starches, Dextrin | 52.4 | 52.5 | 52.8 |

* Cocyl isethionate and sodium lauryl sulfoacetate in equal amounts.

After storage for three months at 37° C. and 45° C. and one year of storage at room temperature it was found that the bar of Example 1 showed minimal discoloration. Assays for hydroquinone indicated little or no oxidation as indicated below, thereby confirming stability. The bars of Examples 2 and 3 were rated satisfactory in terms of organoleptic properties but showed greater discoloration. The bar of Example 1 was used on the skin intermittently over a period of about three(3) weeks and was shown to have skin bleaching properties.

| | Hydroquinone Assay | | |
|---|---|---|---|
| | Initial | 1 Mo./ 45° C. | 6 Mos./ Room Temp. |
| Hydroquinone U.S.P. | 2.2% | 2.2% | 2.2% |

EXAMPLE 4

Skin Bleaching Lotion Formulation

A skin bleaching lotion of this invention, having a pH of about 5, would be obtained if the components listed in Table 2 are blended together.

TABLE 2

| Lotion Formulation | |
|---|---|
| Ingredient | % WT/WT |
| Cetyl Alcohol | 2.0 |
| Numeral Oil Light USP | 2.0 |
| Polyoxyl 40 Stearate | 2.0 |
| Emulsifying Wax NF | 1.0 |
| Glycerin USP | 5.0 |
| Keltrol (Xanthan Gum) | 0.2 |
| Hydroquinone | 2.0 |
| TBHQ | 0.1 |
| Sodium Bisulfite | 0.1 |
| Preservative (Parabens) | 0.4 |
| Fragrance | 0.2 |
| Color | QS 0.2 |
| Water Purified USP | QS 100.0 |

EXAMPLE 5

Skin Bleaching Lotion Formulation

A skin bleaching lotion of this invention, having a pH of about 6, would be obtained if the components of Table 3 are blended together.

TABLE 3

| Lotion Formulation | |
|---|---|
| Ingredient | % WT/WT |
| Stearic Acid, Triple Pressed | 3.0 |
| Cetyl Alcohol | 1.0 |
| Cetyl Palmitate | 2.0 |
| Petrolatum Snow White | 2.0 |
| Diisopropyl Adipate | 2.0 |
| Glycerin USP | 4.0 |
| Sodium Cetearyl Sulfate | 0.5 |
| Sodium Borate | 0.1 |
| Hydroquinone | 2.0 |
| TBHQ | 0.1 |
| Color QS | 0.2 |
| Preservatives | 0.2 |
| Fragrance | 0.2 |
| Water USP QS | 100.0 |

EXAMPLE 6

Skin Bleaching Wax Based Stick

A skin bleaching waxed based stick of this invention would be obtained if the components listed in Table 4 are blended together.

TABLE 4

| Wax Based Stick Formulation | |
|---|---|
| Ingredient | % WT/WT |
| Stearamide MEA monomethanolamide | 26.5 |
| Light Meneral Oil | 5.0 |
| Hydroquinone | 2.0 |
| TBHQ | 0.1 |
| Propoxylated [3] myristyl ether | 25.5 |
| Cyclomethicone | 16.7 |
| Stearyl alcohol | 24.0 |
| Fragrance | 0.2 |

EXAMPLE 7

Skin Bleaching Aerosol

A skin bleaching aerosol of this invention would be otained if the components listed in Table 5 are blended together.

TABLE 5

| Aerosol | |
|---|---|
| Ingredient | % WT/WT |
| Propylene glycol | 1.0 |
| Hydroquinone | 2.0 |
| TBHQ | 0.1 |
| Ethyl alcohol | 56.9 |
| Water | 10.0 |
| Dimethyl Ether (propellant) | 30.0 |

EXAMPLE 8

Skin Bleaching Alcoholic Stick

A skin bleaching alcoholic stick of this invention would be obtained if the components listed in Table 6 are blended together. The resulting product would be placed in an air tight container to prevent alcohol evaporation.

TABLE 6

| Alcoholic Stick | |
|---|---|
| Ingredient | % WT/WT |
| Water, deionized | 15.0 |
| Ethanol SD40 (anhydrous) | 74.4 |
| Hydroquinone | 2.0 |
| TBHQ | 0.1 |
| $C_{12}$-$C_{15}$ Alcohols lactate | 2.0 |
| Sodium Stearate | 6.5 |

Unless stated otherwise, all percents herein are percent by weight of the composition. The total percent of all components in each composition equals 100 percent.

The invention being thus described, it will be obvious that the same may be varied in many ways. Such variations are not to be regarded as a departure from the spirit and scope of the invention and all such modifications are intended to be included within the scope of the claims.

What is claimed is:

1. A skin bleaching skin preparation, excluding detergent bars, comprising:
   (a) hydroquinone in amounts of about 1% to about 5% by weight of the total composition; and
   (b) tertiary butyl hydroquinone in amounts of about 0.1% to about 0.5% by weight of the total composition.

2. The skin preparation of claim 1 wherein said preparation is selected from the group consisting of lotions, creams, aerosols, and solid sticks.

3. A skin preparation of claim 1 additionally comprising a buffer in an amount effective to maintain the pH within a range of about 3.5 to about 7.5.

4. A skin bleaching skin preparation, excluding detergent bars, comprising:
   (a) hydroquinone in amounts of about 1% to about 5% by weight of the total composition;
   (b) tertiary butyl hydroquinone in amounts of about 0.1% to about 0.5% by weight of the total composition; and
   (c) an additional stabilizer in amounts of about 0.05% to about 0.3% by weight of the total composition, wherein said additional stabilizer is selected from the group consisting of sodium sulfite, sodium bisulfite, alpha tocopherol, and mixtures thereof, and wherein the total amount of said tertiary butyl hydroquinone and said additional stabilizer does not exceed about 0.6% by weight of the total composition.

5. The skin preparation of claim 4 wherein said preparation is selected from the group consisting of lotions, creams, aerosols, and solid sticks.

6. The skin preparation of claim 4 additionally comprising a buffer in an amount effective to maintain the pH within a range of about 3.5 to about 7.5.

7. The skin preparation of claim 4 wherein said additional stabilizer is selected from the group consisting of sodium sulfite and sodium bisulfite present in amounts of about 0.05% to about 0.3% by weight of the total composition, alpha tocopherol present in amounts of about 0.1% to about 0.3% by weight of the total composition, and mixtures thereof.

8. The skin preparation of claim 7 additionally comprising a buffer in an amount effective to maintain the pH between about 3.5 and about 7.5.

* * * * *